US009901493B2

(12) United States Patent
Terasoma et al.

(10) Patent No.: US 9,901,493 B2
(45) Date of Patent: Feb. 27, 2018

(54) ABSORBENT ARTICLE

(71) Applicant: UNICHARM CORPORATION, Ehime (JP)

(72) Inventors: Nozomi Terasoma, Kagawa (JP); Toshiyuki Tanio, Kagawa (JP)

(73) Assignee: Unicharm Corporation, Ehime (JP)

( * ) Notice: Subject to any disclaimer, the term of this patent is extended or adjusted under 35 U.S.C. 154(b) by 670 days.

(21) Appl. No.: 14/390,681

(22) PCT Filed: Apr. 2, 2013

(86) PCT No.: PCT/JP2013/060067
§ 371 (c)(1),
(2) Date: Oct. 3, 2014

(87) PCT Pub. No.: WO2013/151039
PCT Pub. Date: Oct. 10, 2013

(65) Prior Publication Data

US 2015/0094681 A1 Apr. 2, 2015

(30) Foreign Application Priority Data

Apr. 6, 2012 (JP) ................................ 2012-086982

(51) Int. Cl.
*A61F 13/15* (2006.01)
*A61F 13/534* (2006.01)
(Continued)

(52) U.S. Cl.
CPC ...... *A61F 13/53436* (2013.01); *A61F 13/534* (2013.01); *A61F 2013/53445* (2013.01);
(Continued)

(58) Field of Classification Search
CPC .............. A61F 13/53436; A61F 13/534; A61F 2013/53445; A61F 2013/53721; A61F 2013/8497
See application file for complete search history.

(56) References Cited

U.S. PATENT DOCUMENTS 7,323,072 B2 1/2008 Engelhart et al.
7,598,428 B2 10/2009 Gustavsson et al.
(Continued)

FOREIGN PATENT DOCUMENTS

CN CN 101686879 A 3/2010
EP 1 290 995 A2 3/2003
(Continued)

OTHER PUBLICATIONS

First Office Action and English translation from corresponding Japanese application No. JP 2012-086982 dated Aug. 25, 2015 (4 pgs).

(Continued)

*Primary Examiner* — Jacqueline Stephens
(74) *Attorney, Agent, or Firm* — Brinks Gilson & Lione

(57) ABSTRACT

An absorbent article that includes: a liquid-permeable topsheet; a liquid-impermeable backsheet; and an absorbent sheet which is arranged between the topsheet and the backsheet and which has a pulp. A plurality of hole portions passing through from the topsheet side to the backsheet side are formed in the absorbent sheet. The topsheet is arranged so as to cover the hole portions of the absorbent sheet. The absorbent sheet has: a plurality of first regions which are bonded with the backsheet at a periphery of the hole portions; and a second region between the plurality of first regions. At least a part of the second region is spaced from the backsheet, and is arranged at the topsheet side more significantly than the first region.

16 Claims, 3 Drawing Sheets

(51) Int. Cl.
*A61F 13/537* (2006.01)
*A61F 13/84* (2006.01)

(52) U.S. Cl.
CPC ............... *A61F 2013/53721* (2013.01); *A61F 2013/8497* (2013.01)

(56) References Cited

U.S. PATENT DOCUMENTS

| | | | |
|---|---|---|---|
| 8,557,068 | B2 | 10/2013 | Mori et al. |
| 2004/0015144 | A1 | 1/2004 | Mori et al. |
| 2005/0148971 | A1 | 7/2005 | Kuroda et al. |
| 2010/0326580 | A1 | 12/2010 | Mori et al. |

FOREIGN PATENT DOCUMENTS

| | | | |
|---|---|---|---|
| EP | 1 348 413 | A1 | 10/2003 |
| JP | S 55-94251 | A | 7/1980 |
| JP | 2002-172139 | A | 6/2002 |
| JP | 2011-104059 | A | 6/2011 |
| WO | WO 2005/004764 | A1 | 1/2005 |

OTHER PUBLICATIONS

European Search Report from corresponding European application No. 13772350.8 dated Oct. 27, 2015 (6 pgs).

Australian Office Action from corresponding Australian application No. 2013244470 dated Oct. 6, 2016 (2 pgs).

First Office Action and English translation from corresponding Chinese application No. 201380018793.3 dated Jun. 4, 2015 (14 pgs).

International Search Report from corresponding PCT application No. PCT/JP2013/060067 dated Jul. 2, 2013 (4 pgs).

Indonesian Office Action from corresponding Indonesian application No. P-00201406610 dated Nov. 6, 2017 (3 pgs).

T
10
30
20
1
31
R1
R2
R1
R1
R2
R1
R1

ABSORBENT ARTICLE

RELATED APPLICATION

This application is a 35 U.S.C. § 371 national phase filing of International Patent Application No. PCT/JP2013/060067, filed Apr. 2, 2013, through which and to which priority is claimed under 35 U.S.C. § 119 to Japanese Patent Application No. 2012-086982, filed Apr. 6, 2012.

TECHNICAL FIELD

The present invention relates to an absorbent article, and in particular, to an absorbent article provided with an absorbent sheet in which a hole portion is formed.

BACKGROUND ART

Conventionally, there are provided a variety of absorbent articles which are capable of improving a feeling of comfort at the time of wearing the absorbent article. For example, in Patent Literature 1, there is provided an absorbent article having a liquid-permeable topsheet, a liquid-impermeable backsheet, and an absorber arranged between the topsheet and the backsheet, wherein holes passing through in a thickness direction of the absorbent article are formed in the absorber (for example, refer to Patent Literature 1).

The absorber of the absorbent article of Patent Literature 1 is an absorber in which a plurality of holes passing through from a skin contact surface side to a non-skin contact surface side are formed in a central excretion region. The plurality of holes are formed so that hole areas in a planar view become constant from the skin contact surface side to the non-skin contact surface side. According to the absorbent article thus configured, a ventilation property can be improved by the holes formed in the absorber.

CITATION LIST

Patent Literature

[PTL 1] Japanese Unexamined Patent Application Publication No. 2011-104059

SUMMARY OF INVENTION

Also, as one of elements to improve a feeling of comfort of a wearer at the time of wearing the absorbent article, flexibility (flexibility in touch sense) is exemplified. For example, the absorber of Patent Literature 1 is an absorber in which the holes are formed to extend in the thickness direction so that hole areas become constant in the thickness direction, the absorber is compressed when it is pressed in the thickness direction, and there is an apprehension that the absorber becomes hard. Accordingly, the absorber becomes hard in touch sense, and there is an apprehension that the feeling of comfort at the time of wearing the absorbent article.

In addition, in order to restrain hardening of the absorber, it is contemplated to reduce a thickness of the absorber. However, if the thickness of the absorber is reduced, a cushion property lowers, and on the contrary, there is an apprehension that the feeling of comfort at the time of wearing is impaired.

The present invention has been achieved in view of the problem, and an object thereof is to provide an absorbent article which is capable of causing the cushion property and the flexibility to be compatible with each other while ensuring a ventilation property.

An aspect of the present invention is summarized as an absorbent article comprising: a liquid-permeable topsheet (10); a liquid-impermeable backsheet (20); and an absorbent sheet (30) which is arranged between the topsheet and the backsheet and which has a pulp, wherein a plurality of hole portions (31) passing through from the topsheet side to the backsheet side are formed in the absorbent sheet, the topsheet is arranged so as to cover the hole portions of the absorbent sheet, the absorbent sheet has: a plurality of first regions (R1) which are bonded with the backsheet at a periphery of the hole portions; and a second region (R2) between the plurality of first regions, and at least a part of the second region is spaced from the backsheet, and is arranged at the topsheet side more significantly than the first region.

DESCRIPTION OF EMBODIMENTS

Figure 1:
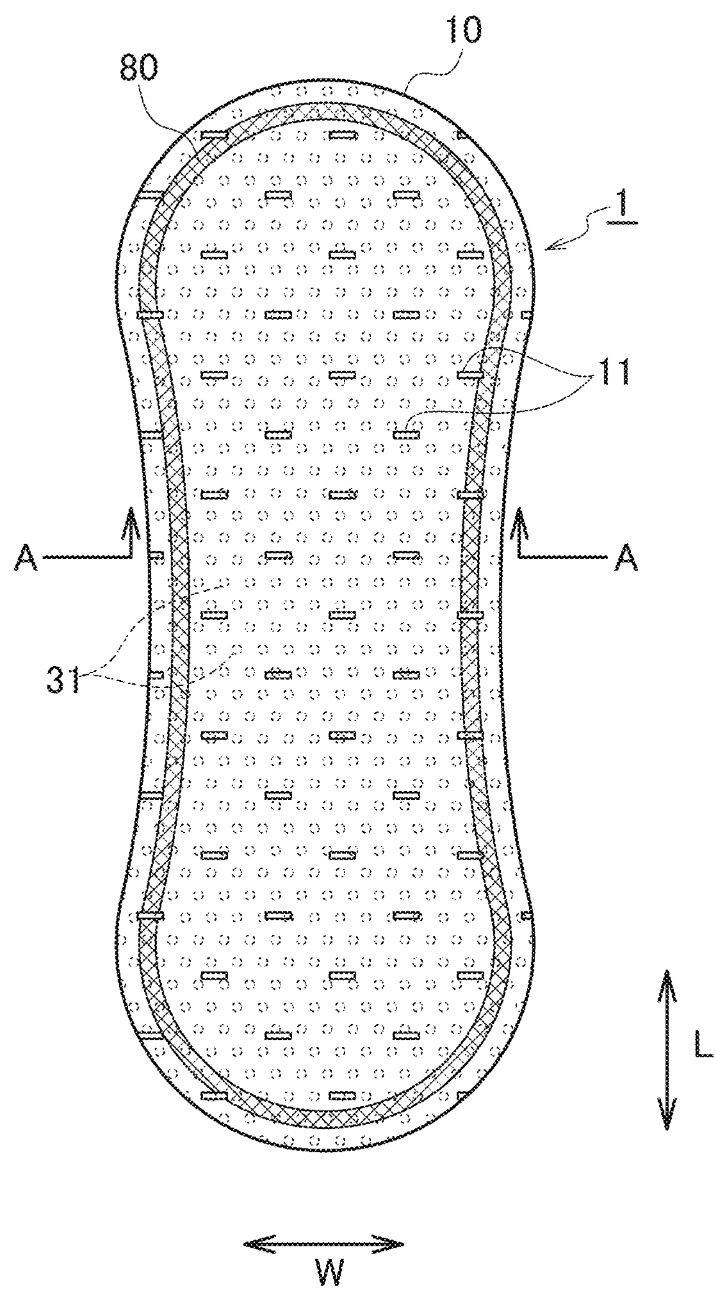
FIG. 1 is a plan view of an absorbent article according to an embodiment is seen from a skin contact surface side.
Figure 2:
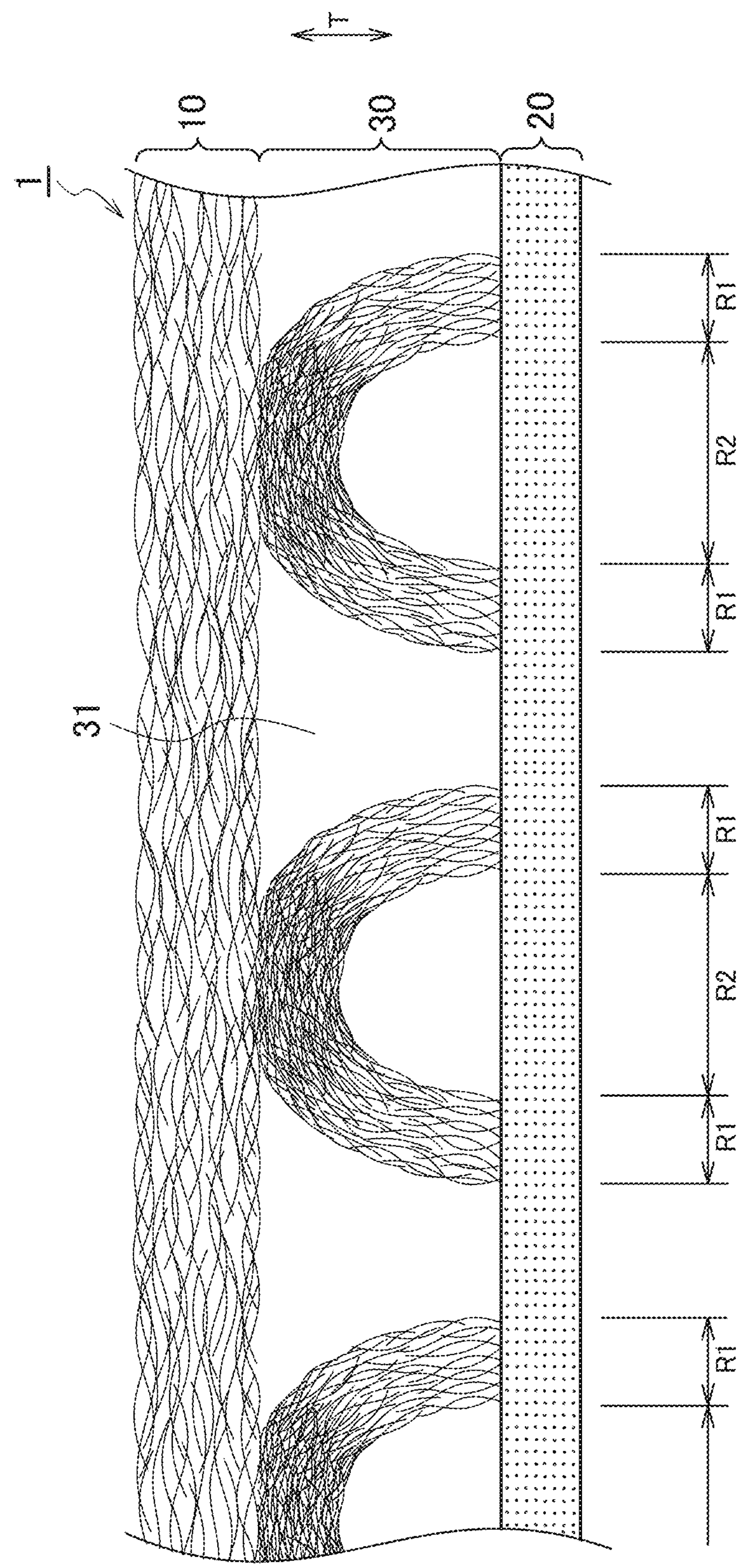
FIG. 2 is a schematic sectional view illustrating, in an enlarged manner, a part of a cross section taken along the line A-A in FIG. 1.

An absorbent article 1 according to an embodiment will be described with reference to the drawings. FIG. 1 is a plan view of the absorbent article, and FIG. 2 is a sectional view taken along the line A-A shown in FIG. 1. The absorbent article 1 according to the embodiment is a vaginal discharge sheet (a panty liner), for example.

The absorbent article 1 has a topsheet 10 that is in contact with the skin of the wearer, a liquid-impermeable backsheet 20 that does not allow liquid to pass through, and an absorbent sheet 30. The absorbent sheet 30 is arranged between the topsheet 10 and the backsheet 20.

The topsheet 10 is a liquid-permeable sheet that allows liquids such as bodily fluid to pass through. The topsheet 10 covers at least the surface of the absorbent sheet 30. The topsheet 10 is not particularly limited as long as the topsheet 10 is a sheet-like material having a structure that allows the liquids to pass through, such as a nonwoven cloth, a woven fabric, a perforated plastic sheet, and a mesh sheet. Natural fibers or chemical fibers can be used as a woven and nonwoven cloth.

A topsheet 10 according to the embodiment is composed of an air-through nonwoven cloth made of a sheath-core fiber of polyethylene and/or polypropylene. More specifically, the fibrous degree of the fiber configuring the air-through nonwoven cloth is 1.7 dtex to 3.3 dtex. A basis weight of the air-through nonwoven cloth is 30 g/m2, a thickness thereof is 2.53 mm, and a density thereof is 0.0138 g/cm3. A topsheet compressed portion 11 which compressed in a thickness direction T is formed on the topsheet 10.

A portion at which the topsheet compressed portion 11 is formed is a portion at which a distance from an absorbent sheet 30 is reduced in comparison with a portion at the periphery of the topsheet compressed portion 11. Accordingly, by forming the topsheet compressed portion 11 on the topsheet 10, a liquid permeation force is locally improved, and an absorption velocity increases. Further, the topsheet compressed portion 11 is formed, whereby irregularities are formed on a surface of the topsheet, and a skin contact area becomes small. Accordingly, the stickiness relative to a skin and a friction between the skin and the topsheet can be reduced.

Incidentally, it is preferable that the topsheet 10 be bulky in order to prevent seepage of a liquid when a load is applied in the thickness direction. Also, it is preferable that a density of the topsheet 10 be lower than a density of the absorbent sheet 30 in order to improve a liquid absorption velocity.

The backsheet 20 has substantially the same length as the length of the topsheet 10. As for the backsheet 20, a polyethylene sheet, a laminated nonwoven cloth nonwoven cloth with polypropylene as the main constituent, an air-permeable resin film, or a sheet in which an air-permeable resin film is joined with a nonwoven cloth such as spun bond or spun lace can be used. It is preferable that the backsheet 20 be made of a material having a flexibility to an extent such that a feeling of discomfort is not felt at the time of wearing the absorbent article, and for example, the backsheet can be used a film obtained from a range of 15 to 30 g/m2 in basis weight, the film consisting essentially of a low density polyethylene (LDPE) resin. It is preferable that the backsheet 20 be liquid-impermeable and moisture-permeable, and for example, the backsheet can be configured with a micro-porous sheet obtained by melt-mixing and kneading an inorganic filler in an olefin resin such as polyethylene or polypropylene and then performing stretch processing of the mixture.

Coloring is applied to an entire surface of the backsheet 20. Accordingly, the entirety of the backsheet 20 functions as a colored portion. Coloring may be formed by kneading a pigment or the like into a material of the backsheet or may be secondarily formed with an ink or the like. In a case where coloring is secondarily applied, it is preferable that the coloring be applied to a skin contact surface side in order to enhance a visual recognition property from the topsheet 10 side.

The absorbent sheet 30 includes a hydrophilic fiber and a pulp. The absorbent sheet 30 is formed of a material capable of absorbing bodily fluids such as vaginal discharge. As examples, there are included: celluloses such as ground pulp or cotton; regenerated celluloses such as rayon or fibril rayon; semi-synthetic celluloses such as acetate or triacetate; particulate polymers; fibrous polymers; thermoplastic hydrophobic chemical fibers or thermoplastic hydrophobic chemical fibers that have been subjected to hydrophilic treatment; and air raid pulps or the like that have been treated with chemical bonding. These can be employed solely or in mixture As the absorbent sheet 30, there is exemplified a pulp sheet obtained by sheeting an absorbent paper or a nonwoven cloth and a fiber with a binder or the like, and as the polymer sheet mentioned above, there is exemplified a sheet or the like formed in the shape of a sheet by mixing a granular polymer in a fiber. Note that, as a sheet formed in the shape of sheet by mixing the granular polymer in the fiber, there can be employed a granular polymer being dispersed in the shape of a layer or being dispersed in a three-dimensional manner.

As the absorbent sheet 30 according to the embodiment, there can be employed a sheet obtained by laminating a material prepared at a ratio of a pulp of 75%, a chemical fiber of 15%, and a spray binder of 10% on the order of a basis weight of 40 g/m2 to 150 g/m2. Also, in the absorbent sheet 30, a plurality of hole portions 31 passing through from the topsheet 10 side to the backsheet 20 side are formed. The hole portions 31 of the absorbent sheet 30 will be described later in detail.

The absorbent sheet 30 is formed in a shape extending in a forward and backward direction, and is identical in dimensions to a respective one of the topsheet 10 and the backsheet 20. The absorbent sheet 30 is adhered to the backsheet 20 by an adhesive such as a hot melt. Note that the absorbent sheet 30 does not need to be identical in dimensions to the respective one of the topsheet 10 and the backsheet 20, and may be configured to be smaller than the respective one of the topsheet 10 and the backsheet 20.

At the backsheet 20, an adhesive (not shown) is applied in a plurality of regions is provided at a surface which is in contact with underwear. The adhesive is provided intermittently along the lengthwise direction L in the backsheet side of the absorbent sheet 30. Before use, an adhesive is in contact with a release sheet not shown in the figures. The release sheet prevents the adhesive from deteriorating before use. At the time of use the absorbent article, the release sheet is peeled off by a wearer.

As for an absorbent article having no release sheet, the absorbent article may be configured to prevent an adhesive from deteriorating before use by a wrapping sheet that is to wrap an individual absorbent article. When the adhesive is in contact with a wrapping sheet, it is preferable to treat the surface of the wrapping sheet so as to make the adhesive releasable without reducing the adhesive strength of the adhesive.

The topsheet, backsheet, and absorbent sheet thus configured are bonded with each other by an adhesive or the like. As a bonding method, it is possible to use any one of heat emboss processing, ultrasonic waves processing, and a hot melt adhesive or a combination of a plurality of approaches. The absorbent article 1 according to the embodiment is an article in which the topsheet 10 and the absorbent sheet 30 are bonded with each other by emboss processing, and the absorbent sheet 30 and the backsheet 20 are bonded with each other by an adhesive. On the topsheet 10 and the absorbent sheet 30, a compressed portion 80 obtained by emboss processing is formed along an outer circumference of the absorbent article 1.

Figure 3:
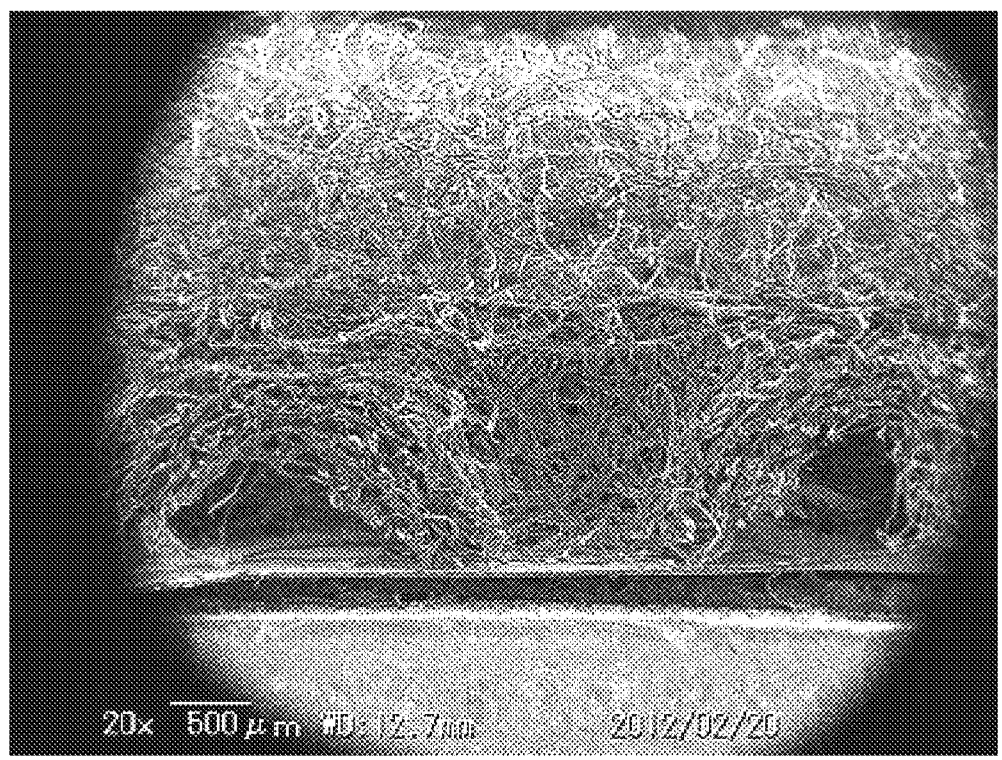
FIG. 3 is a micrographic cross-sectional view of the absorbent article according to the embodiment.

Next, hole portions 31 of the absorbent sheet 30 will be described in detail. FIG. 3 is a micrographic cross-sectional view of the absorbent article according to the embodiment.

In the absorbent sheet 30, a plurality of hole portions 31 passing through from the topsheet 10 side (the skin contact surface side) to the backsheet 20 side (the cloth contact surface side) are formed. The plurality of hole portions 31 are arranged to be spaced in a widthwise direction W and be spaced in a lengthwise direction L all over the absorbent sheet.

Although a diameter of a hole portion 31 is not limited in particular, the diameter can be set to be 1.5 mm to 2.5 mm, for example, from the viewpoints of causing a liquid to be hardly accumulated in the hole portion 31 and ensuring a visual recognition property of a colored portion of the backsheet 20. Also, although the intervals in the widthwise direction W and the lengthwise direction L of the hole portion 31 are not limited in particular, it is preferable that the intervals be on the order of 3.5 mm in the lengthwise direction and on the order of 6.0 mm in the widthwise direction in order to ensure a strength of the absorbent sheet 30.

The absorbent sheet 30 has a first region R1 and a second region R2. As shown in the sectional views of FIG. 2 and FIG. 3, the first region R1 at the periphery of the hole portion 31 of the absorbent sheet 30 is positioned at the backsheet 20 side in a thickness direction T, and the second region R2 between the first region R1 and the first region R1 is positioned at the topsheet 10 side in the thickness direction. The first region R1 is a region which is bonded with the backsheet at the periphery of the hole portion.

At least a part of the first region R1 is spaced from the topsheet 10. At least a part of the second region R2 is spaced from the backsheet 20. Also, a surface of the backsheet 20 side (the non-skin contact side) in the first region R1 is bonded with the backsheet 20, and a surface of the topsheet 10 side (the skin contact surface side) in the second region R2 is bonded with the topsheet 10.

The surface of the non-skin contact side in the first region R1 of the absorbent sheet 30 is bonded with the backsheet 20, and the second region R2 between the first regions R1 is spaced from the backsheet 20. Accordingly, the first region R1 and the second region R2 are arranged to be displaced from each other in the thickness direction. Thus, since the absorbent sheet 30 is arranged to be displaced in the thickness direction for each region, even if there exists a comparatively thin absorbent sheet 30, the dimensions in thickness can be formed to be large, and the cushion property can be ensured.

In addition, since the absorbent sheet 30 is arranged to be displaced in the thickness direction for each region, the absorbent sheet 30 deforms when it is compressed in the thickness direction, whereby an external fore is absorbed, and the hardening of the absorbent sheet 30 can be restrained. Accordingly, the flexibility can also be maintained.

The second region R2 is bonded with the topsheet 10, whereby the first region R1 and the second region R2 are respectively bonded with the backsheet 20 and the topsheet 10, and a positional displacement can be restrained. Accordingly, even if the absorbent sheet 30 deforms, occlusion of the hole portion 31 can be restrained, and a state in which a position between the first region R1 and the second region R2 is displaced in the thickness direction can be maintained.

An opening area of the hole portion 31 in a planar view is reduced as it goes from the topsheet 10 side to the backsheet 20 side. Accordingly, a sectional shape of the hole portion 31 of the absorbent sheet 30 is a tapered shape going to the backsheet 20 side.

The hole portions 31 of the absorbent sheet 30 can be formed by a processing method described below. A hole portion 31 is formed by pinching the absorbent sheet 30 by one pair of plate s. At one plate, a pin for punching the hole portion 31 is protrusively provided, and at the other plate, an opening into which the pin can be inserted is formed. By pinching the absorbent sheet 30 in the thickness direction by such one pair of the plates, the hole portion 31 can be formed while the absorbent sheet 30 is compressed.

When the hole portion 31 passing through in the thickness direction is thus formed in the absorbent sheet 30, there is a need to compress the absorbent sheet 30 in the thickness direction. Accordingly, a density of the absorbent sheet in which the hole portions 31 are formed is higher than a density of the absorbent sheet 30 in which the hole portions 31 are not formed. In particular, a portion in which the hole portions 31 are formed increases in density more significantly than that prior to the processing. As a result, a sparse or dense structure from the topsheet 10 becomes more significant, a liquid absorption velocity from the topsheet 10 to the absorbent sheet 30 increases, and the liquid remaining on the topsheet 10 decreases.

Further, the density of an absorption material configuring the absorbent sheet 30 in the first region R1 is lower than the density of an absorption material configuring the absorbent sheet 30 in the second region R2. According to such configuration, bodily liquid discharged to the topsheet 10 transfers from the topsheet 10 to the second region R2 with its comparatively high density. Accordingly, the bodily liquid can be speedily drawn. Also, in comparison with the densities between the second region R2 and the first region R1, since the density in the second region R2 is higher, the bodily liquid hardly transfers from the second region R2 to the first region R1. Therefore, the bodily liquid hardly enters the hole portions 31 of the absorbent sheet 30.

For example, when the bodily liquid transfers to the hole portions 31, the bodily liquid occasionally reaches the backsheet 20 via the hole portions 31. Since the bodily liquid cannot be retained on the backsheet 20, the bodily liquid remains in the hole portions 31, and the ventilation property is impaired. However, with the absorbent sheet 30 according to the embodiment, accumulation of the bodily liquid in the hole portions 31 is restrained, and the ventilation property can be ensured.

Further, if the bodily liquid enters the hole portions 31, it may be difficult to visually recognize the colored potion of the backsheet 20 from the topsheet 10 via the hole portions 31. However, by restraining the entry of the bodily liquid into the hole portions 31 of the absorbent sheet 30, the visual recognition property of the colored portion can be ensured.

A wearer can visually recognize the colored portion of the backsheet 20 via the topsheet 10 and the hole portions 31 of the absorbent sheet 30, thereby making it possible to visually feel the ventilation property and obtain a sense of security.

Note that it is sufficient if a color tone of the colored potion of the backsheet 20 be capable of visually recognizing the hole portions 31, and the color tone is not limited in particular. However, since an excessively dense color tone is not preferable from the viewpoint of productivity, it is preferable that the hue of the color be reduced to its required minimum. Specifically, it is the most preferable that the color of the colored portion be green, and it is the second preferable that the color be yellow, blue, and red.

In addition, in order to ensure the visual recognition property of the colored portion, it is preferable that the light beam transmittance of the topsheet 10 be 40% to 90%, and it is further preferable that the light beam transmittance be 50% to 90%. Note that, in a case where the topsheet 10 is composed of a plurality of layers, it is preferable that a total light beam transmittance of the plurality of topsheets 10 be in the range mentioned above.

Note that the hardness of the absorbent article can be measured by using the Gurley method stipulated in JIS-1096, for example. Furthermore, the basis weight and density of the absorbent sheet 30 can be measured by the following measurement method, for example. In an absorbent article packaged by a package, the package is opened and the folded absorbent article is expanded, and then the thickness and the area of the portion whose basis weight and density are to be measured are measured. Next, the portion whose basis weight and density are to be measured is cut out from the absorbent article, and then the weight of the cut-out portion is measured. Next, the portions other than the absorbent sheet 30, such as the topsheet 10 and the backsheet, are removed from the cut-out portion, and then the weight of the absorbent sheet 30 is measured. The basis weight is calculated based on the weight of the absorbent sheet 30 and the area of the portion whose basis weight and density are to be measured. The density is calculated based on the basis weight and thickness.

Note that the thickness can be measured by the following measurement method. Specifically, after the sample absorbent article is frozen by immersing it in liquid nitrogen, the sample is cut with a blade, the sample is returned to the normal temperature, and then the resultant sample is measured at 50 times magnification by using a microscope (such as Keyence-make VE7800). Here, the reason for freezing the sample absorbent article is to prevent variation in the thickness due to compression during cutting.

Next, a part of a manufacturing method of the absorbent article 1 according to the embodiment will be described. Note that an existing method can be employed as to a method which is not described herein. In the manufacturing method of the absorbent article, as a first step, a topsheet producing process is carried out. A topsheet is compressed in a thickness direction, and a topsheet compressed portion 11 is formed.

Next, as a second step, an absorbent sheet molding process is carried out. Specifically, by a molding drum, a pulp which is a material for an absorbent sheet is molded and then an absorbent sheet 30 is molded, and a hole portion 31 is opened. Note that the sequential order of the first step and the second step may be reversed in order.

In a third step, a compressing process is carried out. Specifically, the absorbent sheet 30 and the topsheet 10 are compressed in the thickness direction, and a compressed portion 80 is formed.

In a fourth step, a backsheet bonding process is carried out. Specifically, the absorbent sheet and the top sheet or the like, forming the compressed portion and the backsheet 20, are bonded with each other. By the process mentioned above, the absorbent article according to the embodiment can be manufactured.

As described above, although the content of the present invention was disclosed through the embodiments of the present invention, the descriptions and drawings that form a part of this disclosure are not to be considered as limitation to the present invention. From this disclosure, a variety of alternate embodiments, examples, and applicable techniques will become apparent to one skilled in the art.

For example, a sectional shape of a hole portion 31 of the absorbent sheet 30 does not always need to be a tapered shape as it goes from the topsheet 10 side to the backsheet 20 side, and may be a predetermined opening area in the thickness direction.

Note that the backsheet 20 is not always limited to a colored constituent element, and may be white or transparent in color. However, in order to enhance the visual recognition property of the hole portions 31 of the absorbent sheet 30, it is preferable that the backsheet be a colored constituent element (a nonwhite and nontransparent constituent element).

Also, the colored potion may be provided on a surface of a skin contact side of the backsheet as well as the constituent element provided on the backsheet 20, and specifically, the colored portion may be configured by a colored sheet arranged between the absorbent sheet 30 and the backsheet 20 or may be configured by an adhesive to adhere the absorbent sheet 30 and the backsheet 20.

In addition, the absorbent article is not limited to the vaginal discharge sheet, and may be a sanitary napkin or an absorbent pad The entire contents of Japanese Patent Application Laid-open No. 2012-086982 (filed on Apr. 6, 2012) are incorporated in the present specification by reference.

INDUSTRIAL APPLICABILITY

It is possible to provide an absorbent article which is capable of causing a cushion property and flexibility to be compatible with each other while ensuring a ventilation property.

REFERENCE SIGNS LIST

L: lengthwise direction
T: thickness direction
W: widthwise direction
1: absorbent article
10: topsheet
11: topsheet compressed portion
20: backsheet
30: absorbent sheet
31: hole unit
80: compressed portion

The invention claimed is:

1. An absorbent article comprising:
a liquid-permeable topsheet;
a liquid-impermeable backsheet; and
an absorbent sheet which is configured by an absorption material and arranged between the topsheet and the backsheet, and has a pulp, wherein the absorbent sheet is provided with a plurality of hole portions passing through the absorbent sheet in a thickness direction of the absorbent sheet from the topsheet side to the backsheet side,
the topsheet is arranged so as to cover the hole portions of the absorbent sheet,
the absorbent sheet has: a plurality of first regions arranged at a periphery of the hole portions and bonded to the backsheet; and a plurality of second regions, with each second region being located between adjacent ones of the plurality of first regions, and
in the second regions, at least a part of the absorbent material of the absorbent sheet is spaced from the backsheet in the thickness direction to define a space between the backsheet and the absorbent material, and is arranged closer to the topsheet than an absorption material in the first regions bonded to the backsheet.

2. The absorbent article according to claim 1, wherein a surface on the topsheet side in the second regions is bonded with the topsheet.

3. The absorbent article according to claim 2, wherein an opening area of the hole portions in a planer view is reduced as it goes from the topsheet side to the backsheet side.

4. The absorbent article according to claim 3, wherein a density of an absorption material configuring the absorbent sheet in the first regions is lower than a density of the absorption material configuring the absorbent sheet in the second regions.

5. The absorbent article according to claim 4, wherein
the topsheet has light permeability,
the backsheet is provided with a colored portion on a surface of a skin contact side thereof, and
the colored portion of the backsheet is configured to be visually recognizable from a skin contact side of the topsheet via the topsheet and the hole portions of the absorbent sheet.

6. The absorbent article according to claim 3, wherein
the topsheet has light permeability,
the backsheet is provided with a colored portion on a surface of a skin contact side thereof, and the colored portion of the backsheet is configured to be visually recognizable from a skin contact side of the topsheet via the topsheet and the hole portions of the absorbent sheet.

7. The absorbent article according to claim 2, wherein a density of an absorption material configuring the absorbent sheet in the first regions is lower than a density of the absorption material configuring the absorbent sheet in the second regions.

8. The absorbent article according to claim 7, wherein the topsheet has light permeability, the backsheet is provided with a colored portion on a surface of a skin contact side thereof, and the colored portion of the backsheet is configured to be visually recognizable from a skin contact side of the topsheet via the topsheet and the hole portions of the absorbent sheet.

9. The absorbent article according to claim 2, wherein the topsheet has light permeability, the backsheet is provided with a colored portion on a surface of a skin contact side thereof, and the colored portion of the backsheet is configured to be visually recognizable from a skin contact side of the topsheet via the topsheet and the hole portions of the absorbent sheet.

10. The absorbent article according to claim 1, wherein an opening area of the hole portions in a planer view is reduced as it goes from the topsheet side to the backsheet side.

11. The absorbent article according to claim 10, wherein a density of an absorption material configuring the absorbent sheet in the first regions is lower than a density of the absorption material configuring the absorbent sheet in the second regions.

12. The absorbent article according to claim 11, wherein the topsheet has light permeability, the backsheet is provided with a colored portion on a surface of a skin contact side thereof, and the colored portion of the backsheet is configured to be visually recognizable from a skin contact side of the topsheet via the topsheet and the hole portions of the absorbent sheet.

13. The absorbent article according to claim 10, wherein the topsheet has light permeability, the backsheet is provided with a colored portion on a surface of a skin contact side thereof, and the colored portion of the backsheet is configured to be visually recognizable from a skin contact side of the topsheet via the topsheet and the hole portions of the absorbent sheet.

14. The absorbent article according to claim 1, wherein a density of an absorption material configuring the absorbent sheet in the first regions is lower than a density of the absorption material configuring the absorbent sheet in the second regions.

15. The absorbent article according to claim 14, wherein the topsheet has light permeability, the backsheet is provided with a colored portion on a surface of a skin contact side thereof, and the colored portion of the backsheet is configured to be visually recognizable from a skin contact side of the topsheet via the topsheet and the hole portions of the absorbent sheet.

16. The absorbent article according to claim 1, wherein the topsheet has light permeability, the backsheet is provided with a colored portion on a surface of a skin contact side thereof, and the colored portion of the backsheet is configured to be visually recognizable from a skin contact side of the topsheet via the topsheet and the hole portions of the absorbent sheet.

* * * * *